United States Patent
Seki et al.

(10) Patent No.: US 7,331,928 B2
(45) Date of Patent: Feb. 19, 2008

(54) ULTRASONIC DOPPLER BLOODSTREAM MEASUREMENT DEVICE

(75) Inventors: Takao Seki, Yokohama (JP); Hisashi Hagiwara, Yokohama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 284 days.

(21) Appl. No.: 10/534,959

(22) PCT Filed: Feb. 17, 2004

(86) PCT No.: PCT/JP2004/001709

§ 371 (c)(1),
(2), (4) Date: May 16, 2005

(87) PCT Pub. No.: WO2004/073521

PCT Pub. Date: Sep. 2, 2004

(65) Prior Publication Data

US 2006/0122511 A1 Jun. 8, 2006

(30) Foreign Application Priority Data

Feb. 18, 2003 (JP) ............................... 2003-040173

(51) Int. Cl.
*A61B 8/06* (2006.01)
*A61B 8/00* (2006.01)
(52) U.S. Cl. ....................................... 600/454; 600/437
(58) Field of Classification Search ................ 600/437, 600/442, 443, 454, 456, 441; 345/501; 128/916; 711/1; 342/185
See application file for complete search history.

(56) References Cited

U.S. PATENT DOCUMENTS 5,910,117 A * 6/1999 Basoglu et al. ............. 600/454

(Continued)

FOREIGN PATENT DOCUMENTS

JP 5-237107 9/1993

(Continued)

OTHER PUBLICATIONS

"Current Textbook of Ultrasonics in Medicine", vol. 1, edited by The Japan Society of Ultrasonics in Medicine, May 15, 2000, pp. 55-57 (partial translation).

*Primary Examiner*—Eric Winakur
*Assistant Examiner*—Lawrence N Laryea
(74) *Attorney, Agent, or Firm*—Hamre, Schumann, Mueller & Larson, P.C.

(57) ABSTRACT

The present invention is for an ultrasonic Doppler blood flow measurement device with which high-speed computation is possible, even when a memory having the characteristic of different read/write speeds in the row direction and the column direction is used for the buffer memory when computing blood flow information, without being affected by the slower read/write speed. It is provided with a large capacity memory section 10 that is constituted by a memory that has a two-dimensional address space and different data read/write speeds in the row direction and the column direction of that address space, and that stores detection signals, a blood flow computation section 6 that calculates blood flow information from the detection signals, a small capacity memory section 12 that has the capacity of at least the data amount required for the blood flow computation section 6 to compute any one depth point of an object to be examined, and a large capacity memory control section 9 that performs data transfer from the large capacity memory section 10 to the small capacity memory section 12 in the row direction only.

8 Claims, 8 Drawing Sheets

U.S. PATENT DOCUMENTS

| | | |
|---|---|---|
| 6,071,241 A | 6/2000 | Washburn et al. |
| 6,262,749 B1 * | 7/2001 | Finger et al. ............... 345/564 |
| 6,349,143 B1 | 2/2002 | Hastings et al. |

FOREIGN PATENT DOCUMENTS

| | | |
|---|---|---|
| JP | 2000-339441 | 12/2000 |
| JP | 2002-263104 | 9/2002 |

* cited by examiner

ULTRASONIC DOPPLER BLOODSTREAM MEASUREMENT DEVICE

TECHNICAL FIELD

The present invention relates to ultrasonic Doppler blood flow measurement devices that use the Doppler phenomenon of ultrasound to measure blood flow within the body and display an image of the measurement results.

BACKGROUND ART

Figure 7:
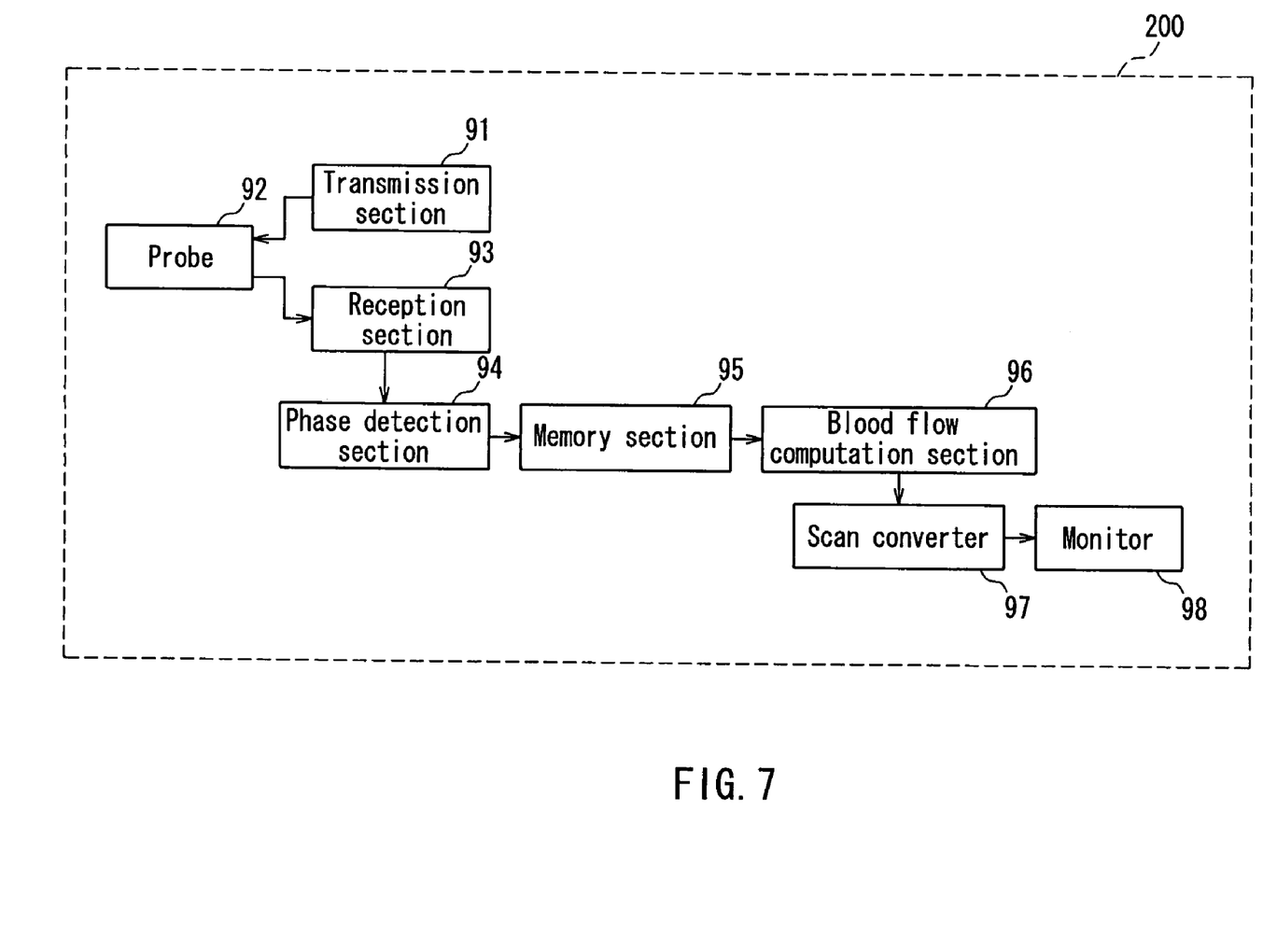
FIG. 7 is a block diagram of a conventional ultrasonic Doppler blood flowmeter.

FIG. 7 shows an example of a conventional ultrasonic Doppler blood flowmeter. A conventional ultrasonic Doppler blood flowmeter 200 shown in FIG. 7 includes a probe 92 that has a plurality of electroacoustic transducer elements and that sends and receives ultrasonic waves, a transmission section 91 that sends transmission signals toward the probe 92, a reception section 93 that applies a delay to the signals that have been changed into electrical signals to produce reception signals, a phase detection section 94 that detects the components that have undergone Doppler transition from among the reception signals and takes these as detection signals, a memory section 95 that stores the detection signals, a blood flow computation section 96 that calculates blood flow information, a scan converter 97 that forms an image, and a monitor 98 that displays an image of the computed results.

An ultrasonic pulsed beam is transmitted N-number of times from the probe 92 toward the object to be examined to the same acoustic line position, and then moved to a next acoustic line position and the same operation is performed. The signals obtained from this scanning pass through the reception section 93 and then are sent to the phase detection section 94. The phase detection section 94 obtains detection signals from the scan signals. The N-number of detection signals that are obtained by transmitting N-number of times to the same acoustic line position are called collectively an "ensemble."

Each detection signal is a signal that is obtained in the depth direction of the object to be examined. The memory section 95 stores one detection signal in one row of memory space. The blood flow computation section 96 reads N-number of data units of the same depth from the memory section 95, that is, reads in the column direction of the memory space, and computes the blood flow information.

Blood flow information corresponding to a single acoustic line position is obtained by repeating this reading task and computation task in the depth direction.

Figure 8:
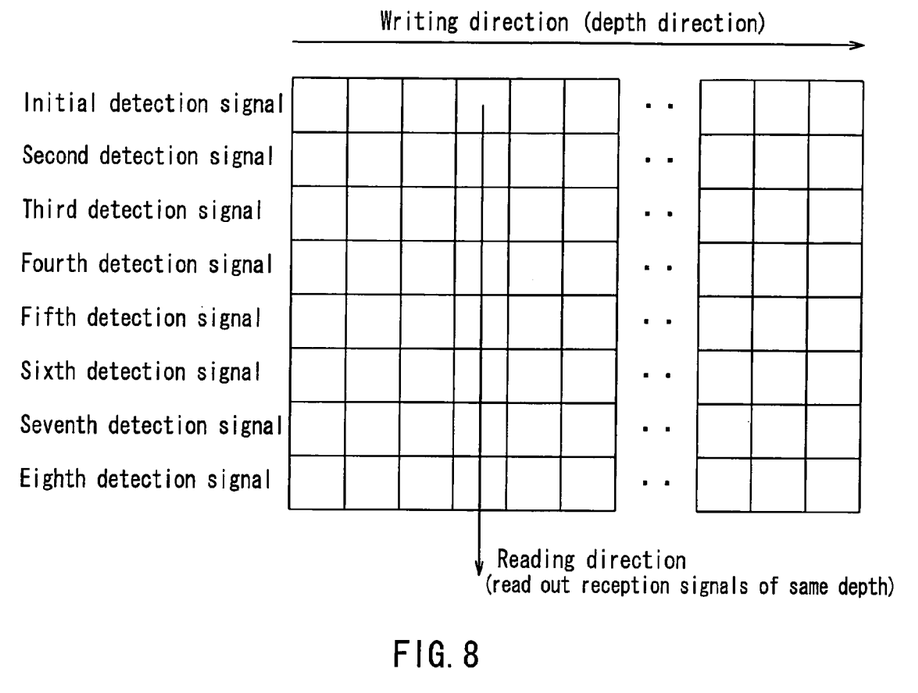
FIG. 8 is a diagram showing the relationship between the writing direction and the reading direction of detection signals to and from the large capacity memory section.

Here, FIG. 8 shows the relationship between the address space of the memory section 95 and the writing direction and reading direction.

The scan converter 97 stores the computer blood flow information results at a site that corresponds to the position of the scan line within the frame memory, and the monitor 98 displays the image information within the frame memory.

Also, the conventional ultrasonic Doppler blood flowmeter 200 has the function of lowering the transmission frequency of the ultrasonic pulses headed toward the same acoustic line position without changing the transmission frequency of the ultrasonic pulsed beams so as to enable observation of low-velocity blood flow without lowering the frame rate (for example, see JP H5-237107A).

Figure 9:
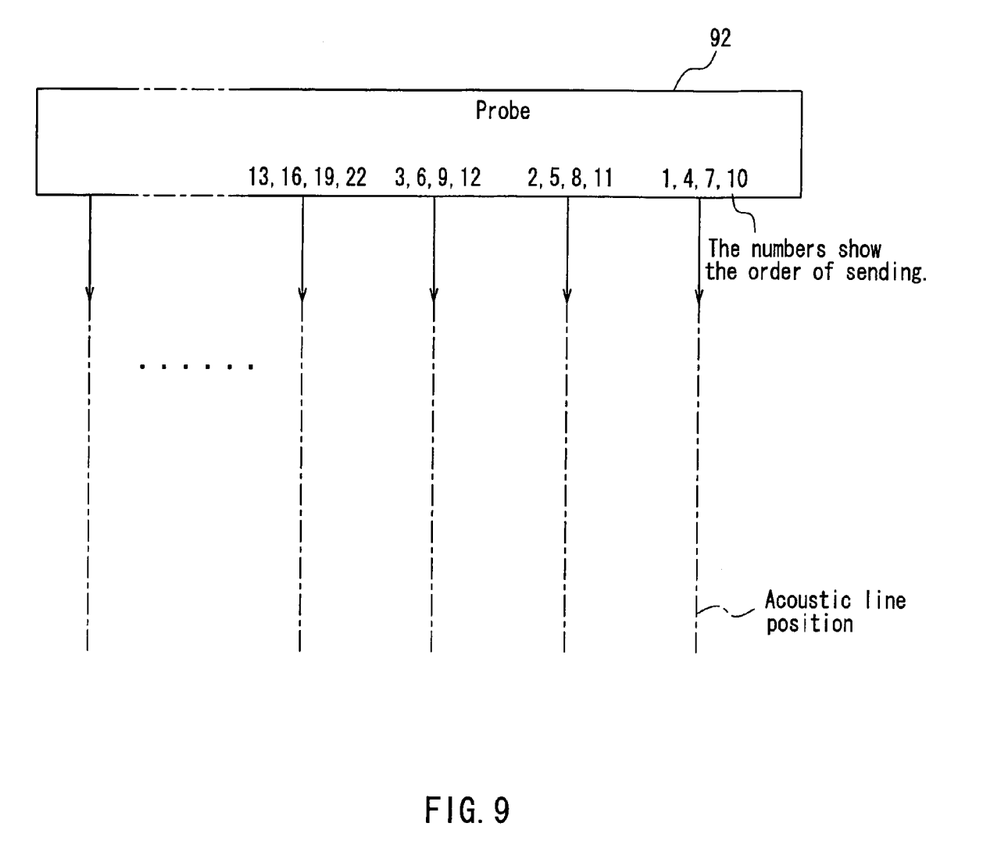
FIG. 9 is a diagram showing the transmission order of the ultrasonic pulses that enable observation of low-velocity blood flow.

This function is achieved by performing transmission of an ultrasonic pulse and reception of the ultrasound pulse echo one time each for the M-number of acoustic line positions in the order of a first acoustic line position, a second acoustic line position, . . . to the M-th acoustic line position, and repeating this task N-number of times to obtain M-number of ensemble data units (FIG. 9 shows the ultrasonic pulsed beam transmission order in the case of M=3, N=4). In order to achieve this function, the capacity of the memory section 95 has at least the capacity of M-number of ensembles (for example, see JP H5-237107A and *New Ultrasound Medicine* 1: *Fundamentals of Medical Ultrasound*, edited by The Japan Society of Ultrasonics in Medicine, first edition, published by Iyo Shoin, May 15, 2000, p. 55-58).

With conventional ultrasonic Doppler blood flowmeters, however, it is necessary to read out the reception signals of the same depth when computing the blood flow velocity, the blood flow velocity dispersion, and the blood flow power, for example, and thus as shown in FIG. 8 it is necessary to read signals in a different direction from the direction in which the data are written to the memory section 95. When using a general inexpensive, compact memory that has the characteristic of different reading speeds in the row direction and the column direction, then the slower reading speed dictates the transfer speed to the blood flow computation section. Consequently, in cases where fast computation was necessary, it was not possible to use memories that have different reading speeds in the row direction and the column direction, and thus it was necessary to use SRAMs.

DISCLOSURE OF THE INVENTION

The present invention was arrived at in order to solve the foregoing conventional problems, and it is an object thereof to provide an ultrasonic Doppler blood flow measurement device that is inexpensive and compact, yet even in a case where the memory used for the memory section has the characteristic of different read/write speeds in the row direction and the column direction, reduces the effects of the slow read/write speed and maintains a transfer speed to the blood flow information computation section that is substantially equivalent to conventional speeds.

To achieve the foregoing object, an ultrasonic Doppler blood flow measurement device is provided with an ultrasonic wave send/receive section that sends ultrasonic pulses into an object to be examined and receives the ultrasonic pulse echoes that are reflected from inside the object, a phase detection section that detects the components that have undergone Doppler transition from among the ultrasound pulse echoes and takes these as detection signals, a first memory section that is constituted by a memory that has a two-dimensional address space and different data read/write speeds in the row direction and the column direction of the address space, and that stores the detection signals, a blood flow information computation section that calculates blood flow information from the detection signals, a second memory section that is constituted by a memory that has a capacity that is smaller than that of the first memory section but is at least the capacity of a data amount required for the blood flow information computation section to compute any one depth point of the object, and that stores the detection signals used for the computation by the blood flow information computation section, and a data transfer section that performs data transfer from the first memory section to the second memory section in only the direction, of the row direction and the column direction of the address space of the first memory section, that has the faster data read/write speed.

With this configuration, data transfer is performed from the first memory section to the second memory section in only the direction, of the row direction and the column direction of the address space of the first memory section, having the faster read/write speed. Thus, even in a case where the memory used for the first memory section has the characteristic of having different read/write speeds in the row direction and the column direction, it is possible to reduce the effects of the slower read/write speed and perform high-speed data transfer to the blood flow information computation section. Consequently, it is possible to provide an ultrasonic Doppler blood flow measurement device that is compact and inexpensive.

In the foregoing configuration, it is preferable that the second memory section is a memory having a capacity that is at least double the data amount necessary for the blood flow information computation section to compute any one depth point of the object, and that the data transfer section transfers the detection signals used for computation of at least two points by the blood flow information computation section from the first memory section to the second memory section.

With this configuration, the second memory section has a capacity with which it is possible to store at least twice the data amount for the blood flow information computation section to calculate any depth point, and thus the data required for computing the blood flow information of two or more points can be transferred together from the first memory section to the second memory section. By collectively transferring the data required for computing blood flow information for two or more points, the number of times that data is read in the fast row direction becomes two or more times per single data transfer. Thus, access in the faster direction increases, allowing the effects of the slow read/write speed side when the blood flow information computation section reads the information of the second memory section to be reduced.

In the ultrasonic Doppler blood flow measurement device of the present invention, it is possible for the first memory section to be constituted by a DRAM or an SDRAM. It is also possible for the second memory section to be constituted by a SRAM.

In the ultrasonic Doppler blood flow measurement device of the present invention, it is possible for the blood flow information computation section, the second memory section, and the data transfer section to be mounted on a single hardware unit, and for the first memory section to be provided as an external memory of the hardware unit. Further, with a configuration in which the operations of the blood flow information computation section and the data transfer section are controlled by a program, it is possible for the operations of the data transfer section, the second memory section, and the blood flow information computation section to be described by software, allowing the operation content to be changed even after the hardware has been installed.

In the foregoing configuration, it is preferable that the blood flow information computation section and the data transfer section are constituted by separate computation processing circuits, and that each computation processing circuit has a direct memory access function with respect to the second memory section. This is because the computation of blood flow information and data transfer can be performed simultaneously, allowing higher-speed processing to be achieved.

A program according to the present invention controls the operations of the blood flow information computation section and the data transfer section mounted onto a single hardware unit as mentioned above. The program executes on the blood flow information computation section and the data transfer section a process of transferring signals that have been input to the hardware unit to the first memory section, a process of determining whether a data amount of the first memory section exceeds a data amount necessary for the blood flow information computation section to compute any one depth point of the object to be examined, a process of performing data transfer from the first memory section to the second memory section, in a case where the result of the determination process is positive, in only the direction, of the row direction and the column direction of the address space of the first memory section, that has the faster data read/write speed, and a process of causing the blood flow information computation section to perform computation using the signals stored on the second memory section.

A program recording medium according to the present invention is a recording medium storing a program that controls the operations of the blood flow information computation section and the data transfer section mounted onto a single hardware unit as mentioned above. The program executes on the blood flow information computation section and the data transfer section a process of transferring signals that have been input to the hardware unit to the first memory section, a process of determining whether a data amount of the first memory section exceeds a data amount necessary for the blood flow information computation section to compute any one depth point of the object to be examined, a process of performing data transfer from the first memory section to the second memory section, in a case where the result of the determination process is positive, in only the direction, of the row direction and the column direction of the address space of the first memory section, that has the faster data read/write speed, and a process of causing the blood flow information computation section to perform computation using the signals stored on the second memory section.

BEST MODE FOR CARRYING OUT THE INVENTION

Hereinafter, embodiments of the ultrasonic Doppler blood flow measurement device according to the present invention are described using the drawings.

First Embodiment

Figure 1:
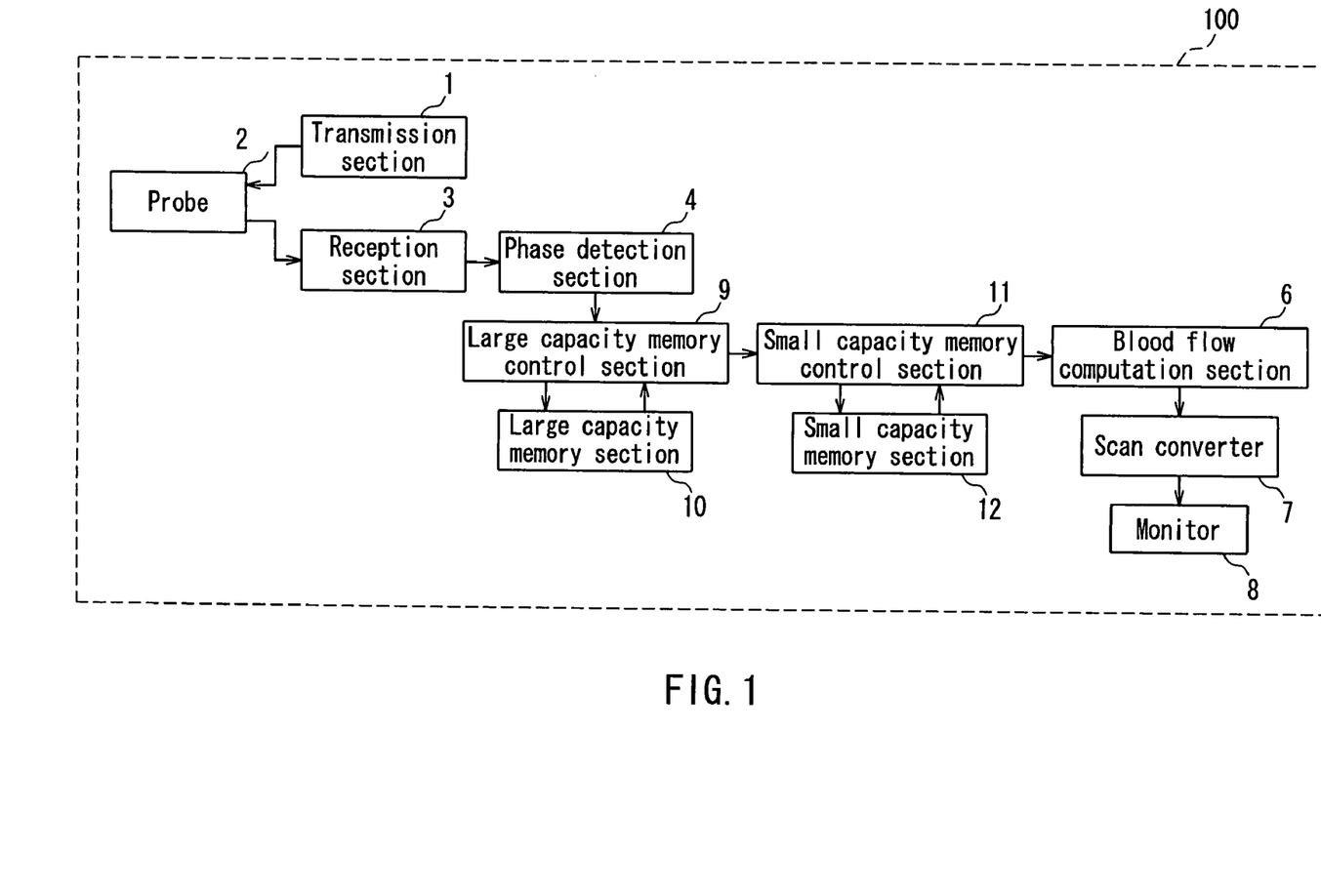
FIG. 1 is a block diagram of an ultrasonic Doppler blood flowmeter according to a first embodiment of the present invention.

FIG. 1 shows the schematic structure of the ultrasonic Doppler blood flowmeter of the first embodiment of the present invention.

As shown in FIG. 1, an ultrasonic Doppler blood flowmeter 100 according to the present embodiment is made of a probe 2 (ultrasonic wave send/receive section) that has a plurality of electroacoustic transducer elements and that sends and receives ultrasonic waves, a transmission section 1 that sends transmission signals toward the probe 2, a reception section 3 that applies delay to the signals that have been changed into electrical signals to produce reception signals, a phase detection section 4 that detects the components that have undergone Doppler transition from among the reception signals and takes these as detection signals, a large capacity memory section 10 (first memory section) that is capable of storing the detection signals of at least two ensembles, a large capacity memory control section 9 (data transfer section) that performs reading and writing with respect to the large capacity memory section 10, a small capacity memory section 12 (second memory section) that has a capacity capable of storing at least one ensemble and stores data necessary for computing the blood flow information, a small capacity memory control section 11 (data transfer section) that performs reading and writing with respect to the small capacity memory section 12, a blood flow computation section 6 that computes blood flow information, a scan converter 7 that forms an image, and a monitor 8 that displays an image of the computer results.

It should be noted that the blood flow information that is computed by the blood flow computation section 6 for example refers to the blood flow velocity, the blood flow velocity dispersion, and the blood flow echo intensity within an object to be examined.

An ultrasonic pulsed beam is transmitted N-number of times to the same acoustic line position from the probe 2 toward the object, and then the next acoustic line position is moved to and the same action is performed. The signals obtained from this scanning are obtained as detection signals from the phase detection section 4 after first passing through the reception section 3. Here, a single ensemble is used to refer collectively to the N-number of detection signals that are obtained by being transmitted N-times to the same acoustic line position. To obtain the data of a single ensemble, if the ultrasound pulsed beam is transmitted and received in the same direction two times, then it is possible to compute a value obtained by synthesizing the blood flow information and the movement information of the tissue, such as organ walls, and if the ultrasound pulsed beam is transmitted and received in the same direction three or more times, then the tissue movement information is suppressed by MTI (moving target indication) and only the blood flow information is computed and output. In this embodiment, N=8 (times) is taken as one ensemble.

Each detection signal is a signal that is obtained in the depth direction of the object to be examined. The large capacity memory control section 9 stores a single detection signal per row of address space within the large capacity memory section 10.

The scan converter 7 stores the computed results of the blood flow information by the blood flow computation section 6 at a site that corresponds to the position of the scan line within the frame memory, and the monitor 8 displays the image information within the frame memory.

By comparing FIG. 1 and FIG. 7 it can be understood that the ultrasonic Doppler blood flowmeter according to this embodiment differs from the conventional ultrasonic Doppler blood flowmeter shown in FIG. 7 primarily in that it is provided with the large capacity memory control section 9, the large capacity memory section 10, the small capacity memory control section 11, and the small capacity memory section 12 in order to store the detection signals that are output by the phase detection section 4.

The memory that is used for the large capacity memory section 10 shall have the characteristic of a fast read/write speed in the row direction and a slow read/write speed in the column direction. For this memory it is for example possible to use a commercially available inexpensive DRAM or SDRAM that is smaller than a SRAM.

On the other hand, the memory used for the small capacity memory section 12 has the characteristic of a fixed access speed, even when performing random access. A SRAM is favorable as a memory for satisfying these conditions.

The detection signals sent from the phase detection section 4 are stored in the large capacity memory section 10 by instruction of the large capacity memory control section 9. At this time, one detection signal (one row worth) is written to the memory space of the large capacity memory section 10 in the direction (row direction) indicated by the arrow "writing direction" in FIG. 2. It should be noted that FIG. 2 expresses the memory space of the large capacity memory section 10. In the drawing the horizontal direction is the row direction and the vertical direction is the column direction, as mentioned earlier, and the large capacity memory section 10 has the characteristic that its read/write speed in the row direction (horizontal direction) is fast and its read/write speed in the column direction (vertical direction) is slow.

Once the final detection signal of a single ensemble (in this embodiment, this consists of eight detection signals) has been written to the large capacity memory section 10, then the large capacity memory control section 9 reads the data of the single ensemble one row at a time from the large capacity memory section 10 and transfers them to the small capacity memory control section 11. It should be noted that the reading direction at this time is indicated by the arrow "reading direction" in FIG. 2, and like the writing direction is the row direction in the large capacity memory section 10.

Figure 3:
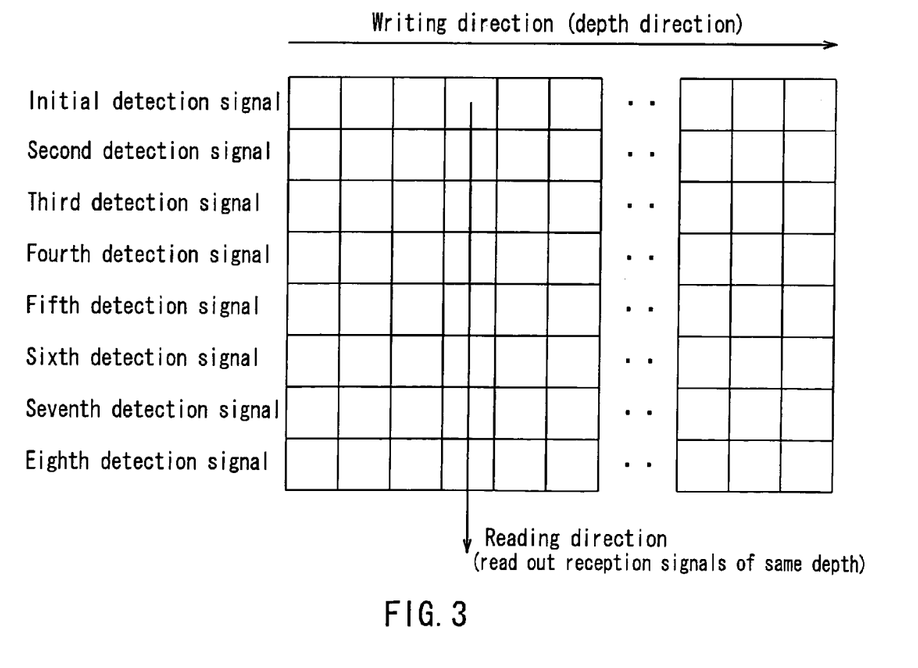
FIG. 3 is a diagram describing the data reading and writing directions of the second memory section (small capacity memory section) in the first embodiment of the present invention.

The small capacity memory control section 11 writes the data of a single ensemble, which have been transferred one row at a time from the large capacity memory section 10, to the small capacity memory section 12. Here, FIG. 3 shows the memory space of the small capacity memory section 12 and the data read/write direction. As shown by the arrow "writing direction" in FIG. 3, the direction in which data are written to the small capacity memory section 12 also is the row direction in the memory space (the horizontal direction in FIG. 3). Once the small capacity memory control section 11 confirms that the transfer of the data of a single ensemble to the small capacity memory section 12 has ended, it reads the detection signals for a same depth (one point) from the data of the ensemble in the small capacity memory section 12 and transfers these to the blood flow computation section 6. The data reading direction at this time is the column direction of the memory space of the small capacity memory section 12 (the vertical direction in FIG. 3) as shown by the arrow "reading direction" in FIG. 3.

Figure 2:
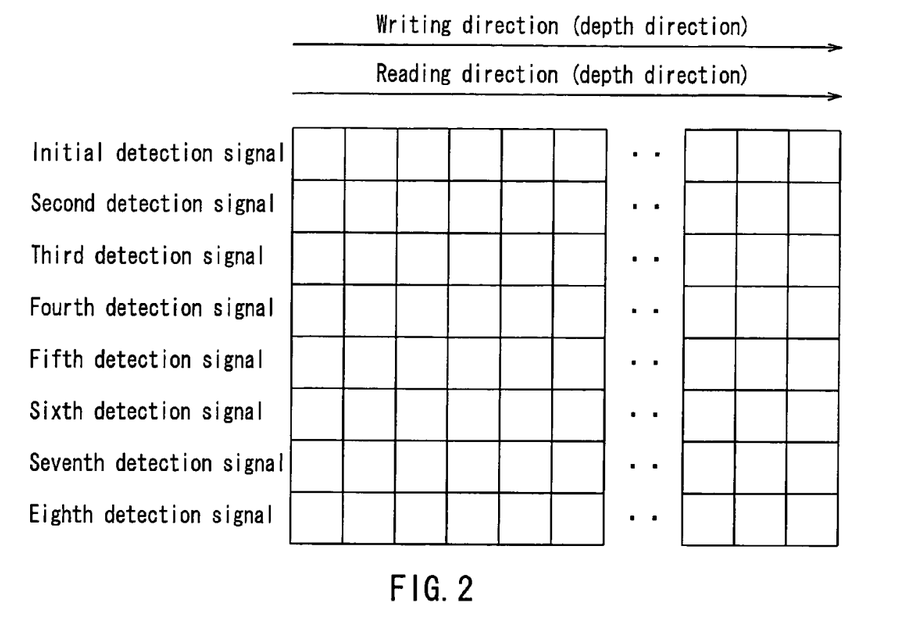
FIG. 2 is a diagram describing the data reading and writing directions of the first memory section (large capacity memory section) in the first embodiment of the present invention.

In this manner, with the ultrasonic Doppler blood flowmeter of the first embodiment a large capacity memory control section 9, a large capacity memory section 10, a small capacity memory control section 11, and a small capacity memory section 12 are provided, and the large capacity memory control section 9 reads and transfers the data of a single ensemble from the large capacity memory section 10 to the small capacity memory section 12 in the row direction only (see FIG. 2). Thus, it is possible to transfer data to the small capacity memory section 12 and the blood flow computation section 6 without being affected by the slow read/write speed of the column direction. Consequently, high-speed data transfer to the small capacity memory section 12 and the blood flow computation section 6 is possible even if the large capacity memory section 10 is constituted by an inexpensive, compact SDRAM.

Also, even in cases where the capacity of the small capacity memory section 12 is the capacity for the detection signals of two points, which are required for the computation of blood flow, rather than for a single ensemble, when the detection signals for the two points have been written to the large capacity memory section 10, then by reading the detection signals for the two points from the large capacity memory section 10 such that they are continuous in the row direction and transferring them to the small capacity memory section 12, the number of continuous readings in the high-speed row direction becomes two, making it possible to reduce the effects of the slow reading speed of the column direction.

Second Embodiment

Figure 4:
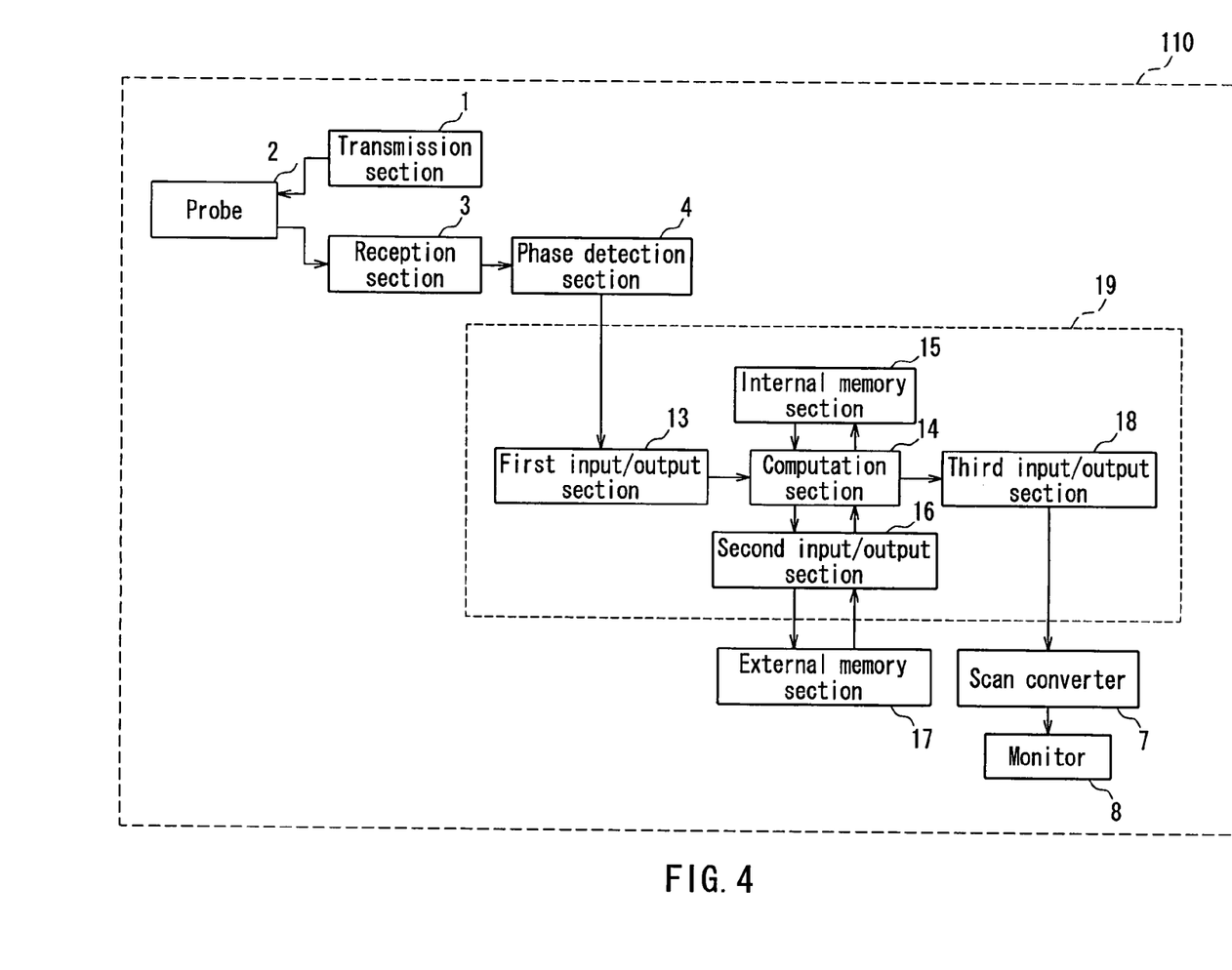
FIG. 4 is a block diagram of an ultrasonic Doppler blood flowmeter according to a second embodiment of the present invention.

FIG. 4 shows the schematic structure of the ultrasonic Doppler blood flowmeter according to a second embodiment of the present invention.

As shown in FIG. 4, an ultrasonic Doppler blood flowmeter 110 according to this embodiment is made of a probe 2 (ultrasonic wave send/receive section) that has a plurality of electroacoustic transducer elements and that sends and receives ultrasonic waves, a transmission section 1 that sends transmission signals toward the probe 2, a reception section 3 that applies delay to the signals that have been changed into electrical signals to produce reception signals, a phase detection section 4 that detects the components that have undergone Doppler transition from among the reception signals and takes these as detection signals, an external memory section 17 (first memory section) that is capable of storing the detection signals of at least two ensembles, a computation unit 19 that inputs and outputs data and performs blood flow information calculation, a scan converter 7 that forms an image, and a monitor 8 that displays an image of the computed results.

The computation unit 19 is formed as a single hardware unit, and is constituted by a first input/output section 13, a second input/output section 16, a third input/output section 18, a computation section 14, and an internal memory section 15 (second memory section).

The first input/output section 13 receives signals from the phase detection section 4. The second input/output section 16 inputs signals from and outputs signals to the external memory section 17. The third input/output section 18 performs output to the scan converter 7. The internal memory section 15 (second memory section) has a capacity that is capable of storing a single ensemble, and stores data that are necessary for blood flow information computation. The computation section 14 has the function of controlling transfer between the internal memory section 15 and the first through third input/output sections, and the function of computing blood flow information.

The structure and operation of the transmission section 1, the probe 2, the reception section 3, the phase detection section 4, the scan converter section 7, and the monitor 8 in FIG. 4 are the same as those in the first embodiment, and thus description thereof is omitted.

By comparing FIG. 4 and FIG. 7 it can be understood that the ultrasonic Doppler blood flowmeter of this present embodiment is different from conventional ultrasonic Doppler blood flowmeters in that the output of the phase detection section 4 is input to the computation unit 19. Also, the computation unit 19 performs input/output to and from the external memory section 17 and performs output to the scan converter 7.

The memory that is used for the external memory section 17 shall have the characteristic of a fast read/write speed in the row direction and a slow read/write speed in the column direction. For this memory it is for example possible to use a compact, inexpensive DRAM or SDRAM, for example.

On the other hand, the memory used for the internal memory section 15 shall have the characteristic of a fixed access speed, even when performing random access. A SRAM is favorable as a memory for satisfying these conditions.

For the computation unit 19 it is possible to use a DSP or a CPU, for example.

Figure 5:
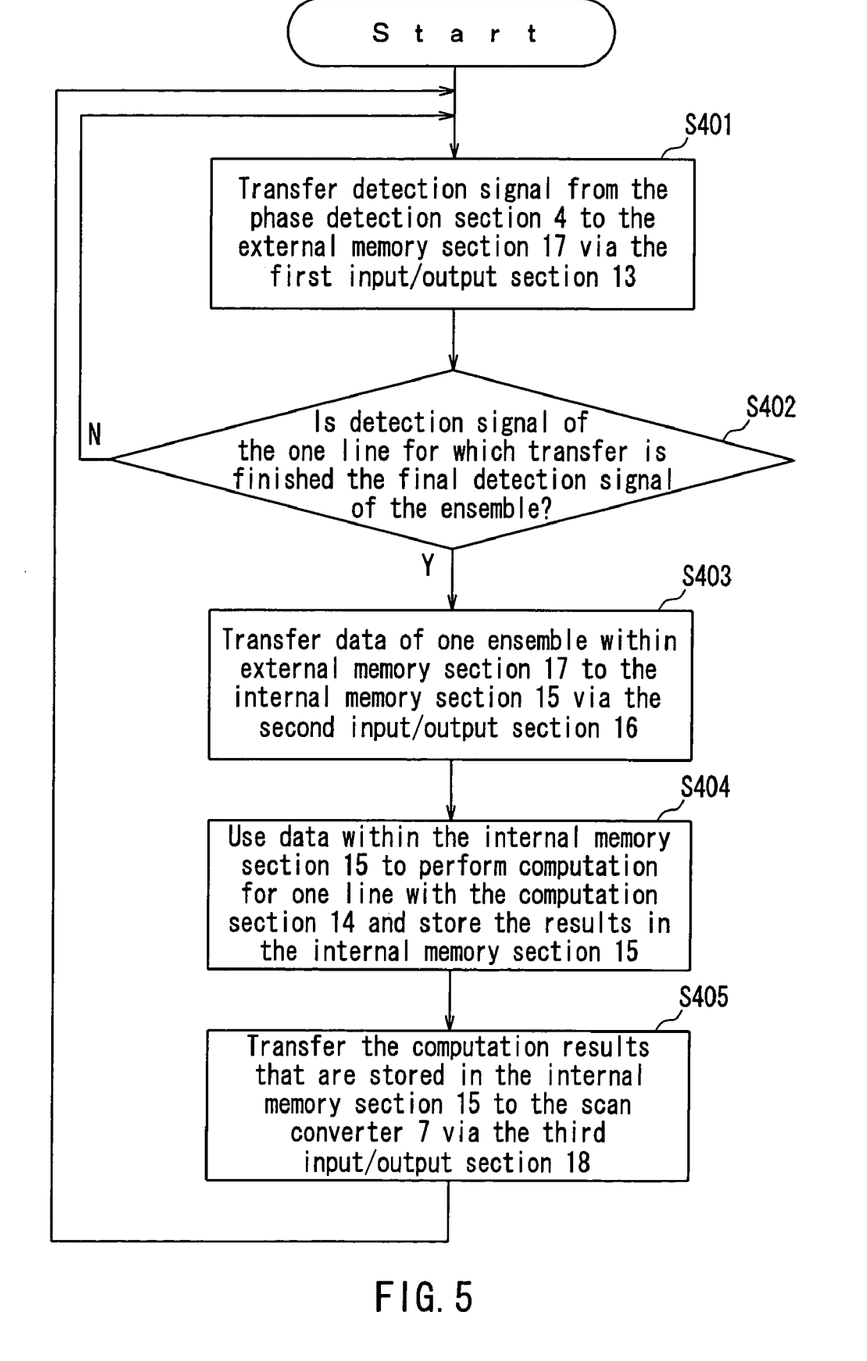
FIG. 5 is a flowchart for describing the operation of the computation unit in the second embodiment of the present invention.

The operation of the ultrasonic Doppler blood flowmeter 110 of this embodiment having the above configuration is described using the flowchart of FIG. 5.

A detection signal that has been sent from the phase detection section 4 to the first input/output section 13 is stored to the external memory section 17 by way of the second input/output section 16 by instruction of the computation section 14. At this time, one detection signal is written to a single row of address space of the external memory section 17 (step S401).

Next, it is determined whether or not the one detection signal that has been written to the external memory section 17 at this time is the final detection signal of the ensemble (step S402). If the result of this determination is NO, then the procedure returns to the process (step S401) of writing from the phase detection section 4 to the external memory section 17. If the result is YES, then the computation section 14 reads the data of the one ensemble from the external memory section 17 one row at a time and transfers them to the internal memory section 15 (step S403). The computation section 14 also reads the data stored on the internal memory section 15, computes the blood flow information for one line, and stores the results of this computation in the internal memory section 15 (step S404).

The computation section 14 then transfers the computation results stored in the internal memory section 15 to the scan converter 7 by way of the third input/output section 18 (step S405), and then the procedure returns to step S401.

In this way, with the ultrasound Doppler blood flowmeter according to the second embodiment, an external memory section 17 and a computation unit 19 having a computation section 14 and an internal memory section 15 are provided, and the computation section 14 with its data transfer function reads and transfers the data of single ensemble from the external memory section 17 to the internal memory section 15 in the row direction only. Thus, it is possible to transfer data to the internal memory section 15 without being affected by the slow read/write speed in the column direction of the external memory section 17.

Moreover, by using a computation unit 19 that has an internal memory section 15, it is possible to use software to describe the operation of the computation section 14, which has the data transfer function and the blood flow computation function, allowing the operation content to be changed even after the hardware has been installed.

Figure 6:
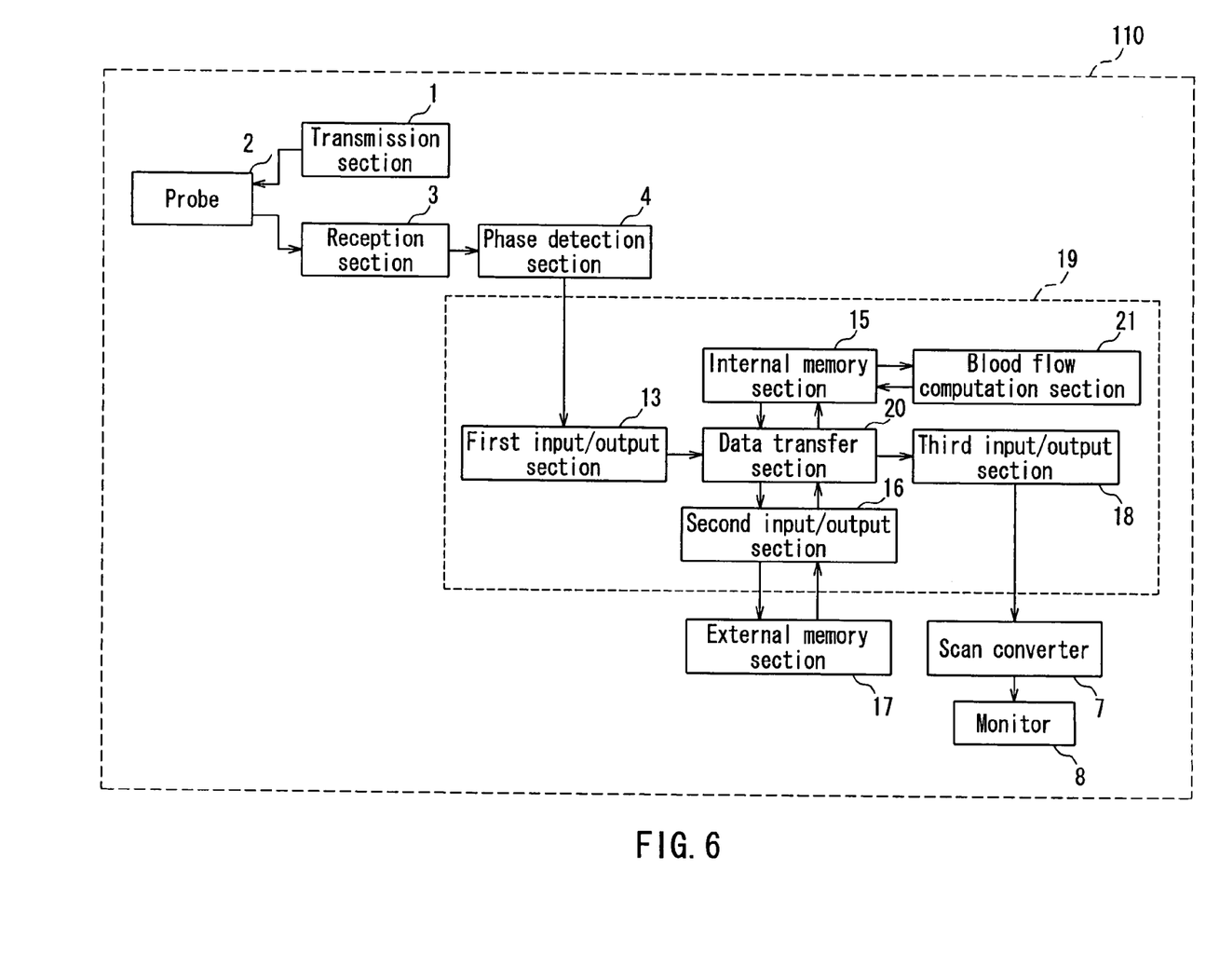
FIG. 6 is a block diagram of an ultrasonic Doppler blood flowmeter according to a modified example of the second embodiment of the present invention.

It should be noted that, as a modified example of the second embodiment, a configuration such as that shown in FIG. 6 also can be considered one embodiment of the present invention. In the configuration shown in FIG. 6, two computation processing circuits (a data transfer section 20 and a blood flow computation section 21) are provided to share the two functions of the computation section 14 shown in FIG. 4 (the data transfer function and the blood flow computation function). By giving the data transfer section 20 and the blood flow computation section 21 the ability to access the internal memory section 15 directly, it becomes possible to perform data transfer while computing the blood flow information, thus allowing faster computation of blood flow information.

In this manner, with the ultrasonic Doppler blood flowmeter of the second embodiment, by reading and transferring the data of a single ensemble from the external memory section 17 to the internal memory section 15 in the row direction only, it is possible to transfer data without being affected by the slow read/write speed in the column direction. Consequently, high-speed data transfer to the internal memory section 15 is possible even if the external memory section 17 is an inexpensive, compact DRAM or SDRAM, for example. It also becomes possible to provide the device more inexpensively.

In the embodiments described above, if the capacity of the small capacity memory section 12 or the internal memory section 15, which are the second memory section, is small, then when transferring from the large capacity memory section 10 or the external memory section 17, which are the first memory section, to the small capacity memory section 12 or the internal memory section 15, which are the second memory section, it is possible to split up the data of a single ensemble and read and transfer the data that have been split up in sequence in the row direction of the memory space of the first memory section. By doing this, it is possible to reduce the effect of the slower read/write speed of the large capacity memory section 10 or the external memory section 17, which are the first memory section, even if the capacity of the small capacity memory section 12 or the internal memory section 15, which are the second memory section, is small.

INDUSTRIAL APPLICABILITY

As shown above, according to the present invention it is possible to provide an ultrasonic Doppler blood flow measurement device that is inexpensive and compact, yet even in a case where the memory used for the memory section has the characteristic of different read/write speeds in the row direction and the column direction, reduces the effects of the slower read/write speed and maintains transfer to the blood flow information computation section that is substantially equivalent to that of convention.

The invention claimed is:

1. An ultrasonic Doppler blood flow measurement device comprising:

an ultrasonic wave send/receive section that sends ultrasonic pulses into an object to be examined and receives ultrasonic pulse echoes that are reflected from inside the object;

a phase detection section that detects components that have undergone Doppler transition from among the ultrasound pulse echoes and takes these as detection signals;

a first memory section that is constituted by a memory that has a two-dimensional address space and different data read/write speeds in a row direction and a column direction of the address space, and that stores the detection signals;

a blood flow information computation section that calculates blood flow information from the detection signals;

a second memory section that is constituted by a memory that has a capacity that is smaller than that of the first memory section but is at least the capacity of a data amount required for the blood flow information computation section to compute any one depth point of the object, and that stores the detection signals used for the computation by the blood flow information computation section; and a data transfer section that performs data transfer from the first memory section to the second memory section in only the direction, of the row direction and the column direction of the address space of the first memory section, that has the faster data read/write speed.

2. The ultrasonic Doppler blood flow measurement device according to claim 1, wherein the second memory section is a memory having a capacity that is at least double the data amount necessary for the blood flow information computation section to compute any one depth point of the object; and wherein the data transfer section transfers the detection signals used for computing at least two points with the blood flow information computation section from the first memory section to the second memory section.

3. The ultrasonic Doppler blood flow measurement device according to claim 1, wherein the first memory section is constituted by a DRAM or a SDRAM.

4. The ultrasonic Doppler blood flow measurement device according to claim 1, wherein the second memory section is constituted by a SRAM.

5. The ultrasonic Doppler blood flow measurement device according to claim 1, wherein the blood flow information computation section, the second memory section, and the data transfer section are mounted on a single hardware unit; and wherein the first memory section is provided as an external memory of the hardware unit.

6. The ultrasonic Doppler blood flow measurement device according to claim 5, wherein the operations of the blood flow information computation section and the data transfer section are controlled by a program.

7. The ultrasonic Doppler blood flow measurement device according to claim 5, wherein the blood flow information computation section and the data transfer section are constituted by separate computation processing circuits; and wherein each computation processing circuit has a direct memory access function with respect to the second memory section.

8. A recording medium storing a program for use in an ultrasonic Doppler blood flow measurement device, the device comprising:

an ultrasonic wave send/receive section that sends ultrasonic pulses into an object to be examined and receives ultrasonic pulse echoes that are reflected from inside the object;

a phase detection section that detects components that have undergone Doppler transition from among the ultrasound pulse echoes and takes these as detection signals; a first memory section that is constituted by a memory that has a two-dimensional address space and different data read/write speeds in a row direction and a column direction of the address space, and that stores the detection signals;

a blood flow information computation section that calculates blood flow information from the detection signals;

a second memory section that is constituted by a memory that has a capacity that is smaller than that of the first memory section but is at least the capacity of a data amount required for the blood flow information computation section to compute any one depth point of the object, and that stores the detection signals used for the computation by the blood flow information computation section; and a data transfer section that performs data transfer from the first memory section to the second memory section in only the direction, of the row direction and the column direction of the address space of the first memory section, that has the faster data read/write speed;

wherein the blood flow information computation section, the second memory section, and the data transfer section are mounted on a single hardware unit;

wherein the first memory section is provided as an external memory of the hardware unit; and wherein the operations of the blood flow information computation section and the data transfer section are controlled by a program, the program executing on the blood flow information computation section and the data transfer section:

a process of transferring signals that have been input to the hardware unit to the first memory section;

a process of determining whether a data amount of the first memory section exceeds a data amount necessary for the blood flow information computation section to compute any one depth point of an object to be examined;

a process of performing data transfer from the first memory section to the second memory section, in a case where the result of the determination process is positive, in only the direction, of the row direction and the column direction of the address space of the first memory section, that has the faster data read/write speed; and a process of causing the blood flow information computation section to perform computation using the signals stored on the second memory section.

* * * * *